(12) United States Patent
Manahilov

(10) Patent No.: US 7,278,742 B2
(45) Date of Patent: Oct. 9, 2007

(54) SYSTEMS AND APPARATUS FOR ASSESSMENT OF VISUAL FIELD FUNCTIONS

(75) Inventor: Velitchko Manahilov, Glasgow (GB)

(73) Assignee: University Court of Glasgow Caledonian University (GB)

( * ) Notice: Subject to any disclaimer, the term of this patent is extended or adjusted under 35 U.S.C. 154(b) by 815 days.

(21) Appl. No.: 10/656,680

(22) Filed: Sep. 5, 2003

(65) Prior Publication Data

US 2004/0087868 A1 May 6, 2004

(30) Foreign Application Priority Data

Sep. 6, 2002 (GB) ................. 0220721.5

(51) Int. Cl.
A61B 3/02 (2006.01)
(52) U.S. Cl. .................. 351/224; 351/237; 351/246
(58) Field of Classification Search ........ 351/222–224, 351/237–239, 243, 246
See application file for complete search history.

(56) References Cited

U.S. PATENT DOCUMENTS

| 5,440,360 | A | * | 8/1995 | Torrey et al. ............. 351/239 |
| 5,912,723 | A | | 6/1999 | Maddess .................. 351/246 |
| 6,213,956 | B1 | | 4/2001 | Lawton .................... 600/558 |
| 2003/0081176 | A1 | * | 5/2003 | Stewart ................... 351/223 |

FOREIGN PATENT DOCUMENTS

| WO | WO99/58046 | 11/1999 |
| WO | WO 02/00106 A1 | 1/2002 |

OTHER PUBLICATIONS

Lachenmayr, et al., "Perimetry and its Clinical Correlations", Thieme Medical Publishers, Inc. New York (1993).
McIlwain, Experimental Brain Research 1, 265-271 (1966).
Ikeda, et al., Vision Res. vol. 12, pp. 1857-1879, Pergamon Press (1972).
Fischer, et al., Brain Research, 21, pp. 225-227 (1974).
Barlow, et al., J. Physiol. 269, pp. 177-194 (1977).

(Continued)

*Primary Examiner*—Huy Mai
(74) *Attorney, Agent, or Firm*—George N. Chaclas; Edwards Angell Palmer & Dodge, LLP

(57) ABSTRACT

Systems, apparatus and associated methods for use in the assessment of visual field functions. In particular, perimetry testing and visual evoked potential (VEP) testing is performed by a visual display device adapted to display visual stimulus patterns and a means for generating visual stimulus patterns within a predetermined visual field and for controlling the display of said visual stimulus patterns by said visual display device, wherein the means for generating visual stimulus patterns is adapted to generate a test stimulus for display in a central region of the visual field and to generate an inducing stimulus for display in a peripheral region of the visual field, and to control the visual display device so as to selectively display the test stimulus alone and in combination with the inducing stimulus in accordance with a predetermined test protocol.

19 Claims, 3 Drawing Sheets

OTHER PUBLICATIONS

Breitmeyer, et al., "Local Foveal Inhibitory Effects of Global Peripheal Excitation", Science, vol. 203, pp. 463-465, Feb. 2, 1979.

Breitmeyer, et al., Vision Research, vol. 20, pp. 799-805, Pergamon Press Ltd 1980.

Valberg, et al., Vision Research, vol. 20, pp. 789-798, Pergamon Presd Ltd. 1980.

Valberg, et al., Vision Research, Vo. 21, pp. 947-950, Permagon Press Ltd. 1981.

Hjorth, Electroencephalography and Clinical Neurophysiology, vol. 39, 526-530 (1975).

Manahilov, et al., Electroencephalography and Clinical Neurophysiology, vol. 82, pp. 220-224 (1992).

Tolhurst, et al., Vision Research, vol. 23, No. 8., pp. 775-785, Pergamon Press Ltd. (1983).

Skoczenski, et al., Nature, vol. 391112, Feb. 1998.

\* cited by examiner

SYSTEMS AND APPARATUS FOR ASSESSMENT OF VISUAL FIELD FUNCTIONS

CROSS-REFERENCE TO RELATED APPLICATION

This application claims priority to U.K. Patent Application No. GB0220721.5, filed Sep. 6, 2002, which is incorporated herein by reference.

BACKGROUND OF THE INVENTION

The present invention relates to systems, apparatus and associated methods for use in the assessment of visual field functions. In its various aspects, the invention if particularly concerned with perimetry testing and visual evoked potential (VEP) testing.

Perimetry is the systematic measurement of visual field function. It is used in diagnosing different diseases in the eye, optic nerve and central nervous system. The conventional methods for assessment of visual defects of peripheral vision are based on measurement of responses to visual stimuli presented at various locations in the visual field. Several techniques use this approach:

(i) White-on-white (W-W) perimetry detects visual field impairments by measuring the sensitivity to a small luminance target presented on a homogenous background. The two most commonly used types of W-W perimetry are Goldmann kinetic perimetry and threshold static automated perimetry. With Goldmann or "kinetic" perimetry, a trained perimetrist moves the target whose brightness is held constant. The limits of the visual field are mapped for targets of different sizes and brightness. With threshold static automated perimetry, a computer program is dimmest target the patient can see at each of the test locations is found. The data are used to construct a map of the visual sensitivity of the retina.

(ii) Short wavelength automated perimetry (SWAP) utilises a blue stimulus to preferentially stimulate the blue cones. A high luminance yellow background is used to adapt to green and red cones and to saturate, simultaneously, the activity of the rods.

(iii) Frequency-doubling perimetry (FDP) uses rapidly flickering gratings. These stimuli create an illusion (apparent doubling of grating spatial frequency) that allows only a small set of retinal ganglion (M cells) cells to respond.

These techniques reveal visual defects by comparing patients' results with those obtained with normal observers. A disadvantage of these approaches is that visual sensitivity is measured by psychophysical procedures which usually depend on the criterion used by the observers. This might result in large interindividual differences which reduce the sensitivity of the measurements.

Objective techniques have also been developed:

(i) Multifocal electoretinogram (ERG) perimetry. ERGs are electrical signals generated by retinal cells in response to a visual stimulus. MERGs are elicited by a pseudorandom binary m-sequence of luminance patches. The luminance of each sector of a dartboard-like pattern alternates between white and black. MERGs elicited by different patches are analysed by a reverse correlation technique in order to construct a map of the responses of retinal cells.

(ii) Multifocal visual evoked potential (VEP perimetry. VEPS are electrical signals generated by cortical cells in response to a visual stimulus. The stimulation is also based on a pseudo-random binary m-sequence of visual targets presented in different visual-field locations. A reverse correlation technique is used to analyse the data.

It is known that the visual cortex has an expanded representation of the fovea because of the high density of ganglion cells in the fovea. The fovea is represented on the surface of the brain. The activity of this area can be recorded by scalp electrodes. The primary visual cortex representing the peripheral parts of the visual field, however, is folded in deeper areas of the brain. These areas of the primary visual cortex contribute little to the VEPs.

One aspect of the present invention concerns long-distance perimetry, providing new systems, apparatus and associated methods for assessment of visual-field defects which are based on measurement of long-distance interactions between an "inducing" stimulus and a "test" stimulus.

The term "long-distance interactions" usually refers to interactions between the responses to two stimuli whose separation is larger than the receptive field size. Electrophysiological studies have shown that the responses of cells in cat and monkey retina, lateral geniculate nucleus and visual cortex can be affected by a moving or shifting luminance pattern outside their receptive fields [refs.2-5]. Psychophysical data also have shown that the threshold visibility of a foveal test spot was reduced when a luminance grating is jerked in the periphery of the visual field [refs.6-8]. Measurements of visual evoked potentials (VEPs) in humans have demonstrated that the contrast reversal of a structured image reduced the magnitude of the VEPs elicited by a foveal stimulus.

One possible explanation of these findings is that long-distance interactions between the peripheral inducing stimulus and the test stimulus may increase the neural internal noise of the cells which are involved in the detection of the test pattern. The increased. internal noise will require a stronger signal in order to maintain a given level of visibility. Another possible explanation is based on the assumption that the long-distance interactions result in cortical transient-to-sustained neurone inhibition.

SUMMARY OF THE INVENTION

One aspect of the present invention uses the phenomenon of long-distance interactions as a perimetric tool. In essence, a flashing peripheral stimulus reduces the response to a central test spot if the peripheral location has normal functioning. Lack of effect points to a loss of visual function at the peripheral location. The long-distance effect is estimated by methods of psychophysics and visual evoked potentials.

In accordance with a first aspect of the invention, there is provided apparatus for use in the assessment of visual field functions, including:

a visual display device adapted to display visual stimulus patterns; and a means for generating visual stimulus patterns within a predetermined visual field and for controlling the display of said visual stimulus patterns by said visual display device; wherein:

said means for generating visual stimulus patterns is adapted to generate a test stimulus for display in a central region of the visual field and to generate an inducing stimulus for display in a peripheral region of the visual field, and to control the visual display device so as to selectively display the test stimulus alone and in combination with the inducing stimulus in accordance with a predetermined test protocol.

Preferably the means for generating visual stimulus patterns is a computer. Preferably, the visual display device is a plasma monitor.

In embodiments for use in electrophysiological testing, the apparatus preferably further includes:
test electrodes for detecting VEPs in response to visual stimuli displayed by said display device; and
a recording device adapted to record VEP signals from said test electrodes and to compare VEP signals generated in response to the display of the test stimulus alone with VEP signals generated in response to the display of the test stimulus in combination with the inducing stimulus.

Preferably the recording device is in the form of a second computer. In another embodiment, there are three test electrodes. Preferably, the computer is adapted to calculate a Laplacian response (second spatial derivative of the potential field distribution) from each set of VEP signals.

Preferably, the computer is adapted to calculate a ratio of the Laplacian response for the test stimulus alone and the Laplacian response for the combination of the test stimulus and inducing stimulus.

In embodiments for use in psychophysical testing, the apparatus preferably further includes:
control means operable by a test subject for increasing and decreasing the contrast of the visual stimulus displayed by the display device and for indicating a threshold contrast value.

Preferably, the computer is adapted to execute a test protocol comprising: generating a first visual stimulus; recording a first threshold contrast value indicated by the test subject using the control means; displaying the stimulus again with a contrast equal to a randomly selected multiple of the first threshold contrast; recording a second threshold contrast value indicated by the test subject using the control means; repeating this process for a predetermined number of iterations; and calculating a mean threshold contrast value from said first, second and subsequent threshold contrast values.

Preferably, the computer is adapted to calculate a mean threshold value for a stimulus comprising the test stimulus alone and a stimulus comprising the combination of the test stimulus and inducing stimulus, and to calculate the ratio of these two mean threshold values.

In accordance with a second aspect of the invention, there is provided a method for assessing visual field functions, comprising:
displaying visual stimulus patterns within a predetermined visual field using a visual display device, said visual stimulus patterns comprising a test stimulus displayed in a central region of the visual field and an inducing stimulus displayed in a peripheral region of the visual field; and selectively displaying the test stimulus alone and in combination with the inducing stimulus in accordance with a predetermined test protocol.

Preferably, the visual display device is a plasma monitor.

In embodiments for use in electrophysiological testing, the method preferably further includes:
deploying at least three test electrodes for detecting VEPs in response to visual stimuli displayed by said display device; and
recording VEP signals from said test electrodes and comparing VEP signals generated in response to the display of the test stimulus alone with VEP signals generated in response to the display of the test stimulus in combination with the inducing stimulus.

Preferably, the method includes calculating a Laplacian response (second spatial derivative) from each set of VEP signals and calculating a ratio of the Laplacian response for the test stimulus alone and the Laplacian response for the combination of the test stimulus and the inducing stimulus.

In embodiments for use in psychophysical testing, the method preferably further includes:
the test subject operating control means to increase and decrease the contrast of the visual stimulus displayed by the display device and to indicate a threshold contrast value.

Preferably, the method includes a test protocol comprising: generating a first visual stimulus; recording a first threshold contrast value indicated by the test subject using the control means; displaying the stimulus again with a contrast equal to a randomly selected multiple of the first threshold contrast; recording a second threshold contrast value indicated by the test subject using the control means; repeating this process for a predetermined number of iterations; and calculating a mean threshold contrast value from said first, second and subsequent threshold contrast values.

Preferably, the method further includes calculating a mean threshold value for a stimulus comprising the test stimulus alone and a stimulus comprising the combination of the test stimulus and inducing stimulus, and calculating the ratio of these two mean threshold values.

In accordance with a third aspect of the invention, there is provided apparatus for use in the assessment of visual field functions, comprising:
a visual display device adapted to display visual stimulus patterns;
a computer adapted to generate visual stimulus patterns within a predetermined visual field and to control the display of said visual stimulus patterns by said visual display device, said computer being adapted to generate test stimuli for display in a first region of the visual field and to generate visual Gaussian noise patterns of different noise densities for display in at least one other region of the visual field, and to control the value display device so as to selectively display the test stimulus alone and in combination with the noise pattern in accordance with a predetermined test protocol;
at least three test electrodes for detecting VEPs in response to visual stimuli displayed by said display device; and
a computer adapted to record VEP signals from said test electrodes, to calculate a Laplacian response (second spatial derivative) from each set of VEP signals, and to derive an internal neural noise value for said first region of the visual field from said Laplacian responses and associated Gaussian noise densities.

In accordance with a forth aspect of the invention, there is provided a method for assessing visual field functions, comprising:
generating visual stimulus patterns within a predetermined visual field using a visual display device, said stimulus patterns comprising test stimuli displayed in a first region of the visual field and visual Gaussian noise patterns of differing noise densities displayed in at least one other region of the visual field; and selectively displaying the test stimulus alone and in combination with the noise pattern in accordance with a predetermined test protocol;

deploying at least three test electrodes for detecting VEPs in response to visual stimuli displayed by said display device; and recording VEP signals from said test electrodes, calculating a Laplacian response (second spatial derivative) from each set of VEP signals, and deriving an internal neural noise value for said first region of the visual field from said Laplacian responses and associated Gaussian noise densities.

BRIEF DESCRIPTION OF THE DRAWINGS

Embodiments of the invention will now be described, by way of example only, with reference to the accompanying drawings, in which.

DETAILED DESCRIPTION OF PREFERRED EMBODIMENTS

Figure 1:
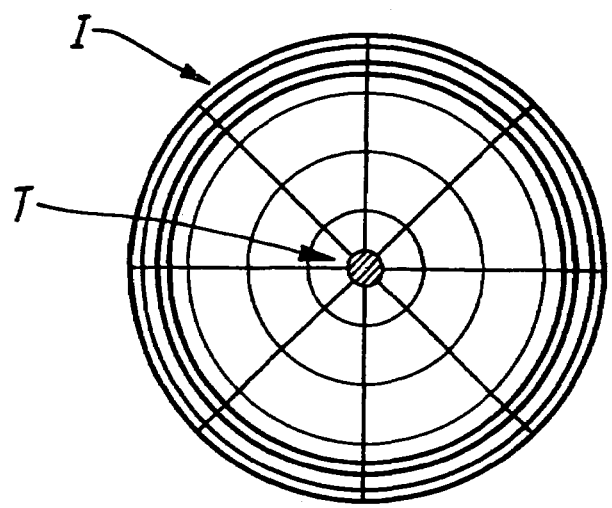
FIG. 1 is a diagram illustrating one example of the type of visual stimuli employed in embodiments of the present invention.

Referring now to the drawings, FIG. 1 shows one example of the type of stimuli used for the purposes of the invention. The drawing illustrates the visual field as a circular dartboard pattern, with an "inducing stimulus" I comprising a series of concentric circles around the periphery of the field and a "test stimulus" T comprising a circular visual checkerboard or noise pattern at the centre of the field. It will be understood that the nature of these stimuli may vary widely. In particular, the inducing stimulus I may vary in terms of its location within the visual field, the type of pattern and the dynamics of the stimulus (generally, the stimuli will comprise time varying patterns, typically including flashing or contrast reversal at a particular frequency). The stimuli are discussed further below.

Figure 2:
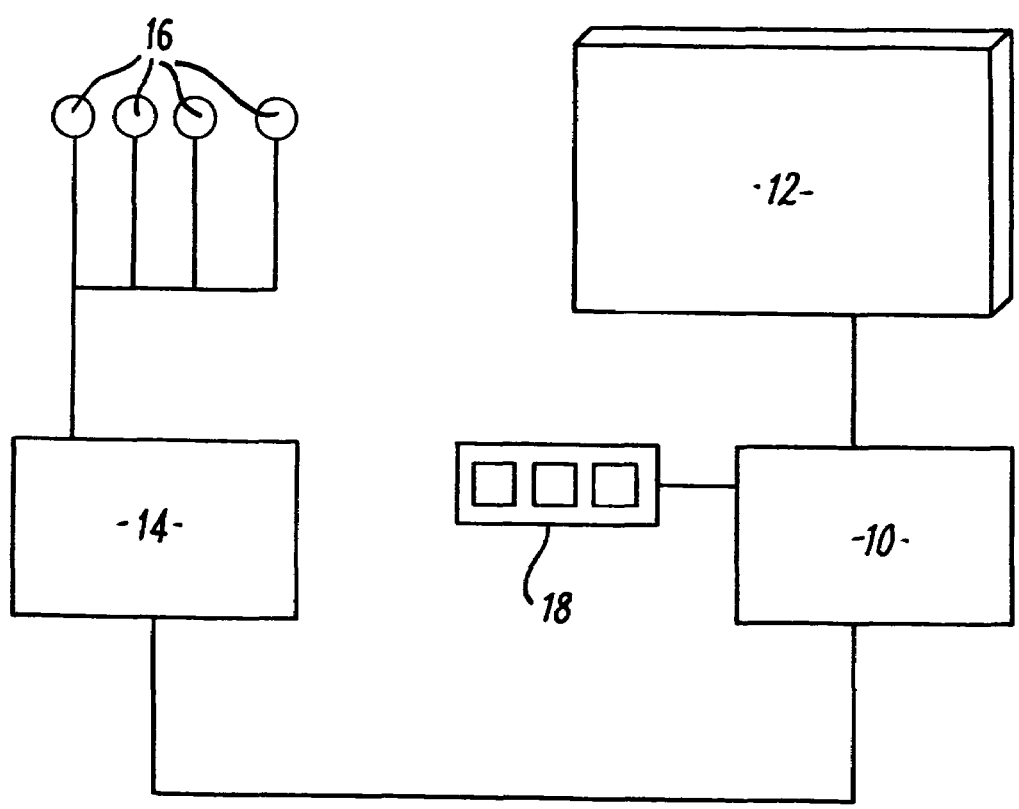
FIG. 2 is a block diagram illustrating apparatus in accordance with one embodiment of the present invention.

The stimuli are generated by a first computer 10 (FIG. 2) and presented by means of any suitable visual display apparatus 12. The visual display apparatus 12 may comprise any of a variety of will known display devices, including cathode ray tubes, LCD displays, video projectors etc. It is preferred that the display area is relatively large in order to allow a reasonable distance between the test subject and the display. It is particularly preferred that the display 12 comprises a plasma type monitor, which provides a large display area and instantaneous screen updates (as compared with raster-scan type displays).

As noted above, the first computer 10 generates the stimuli and controls the display apparatus 12. When the invention is applied for electrophysiological testing, the apparatus further includes a second computer 14, connected to electrodes 16 for detecting the subject's neural responses, which records and processes signals from the electrodes 16, as described further below. The first and second computers 10 and 14 are connected to enable the correlation of stimuli and responses. Alternatively, the functions of the first and second computers may be performed by a single computer or by any other suitable arrangement of computers.

Figure 4:
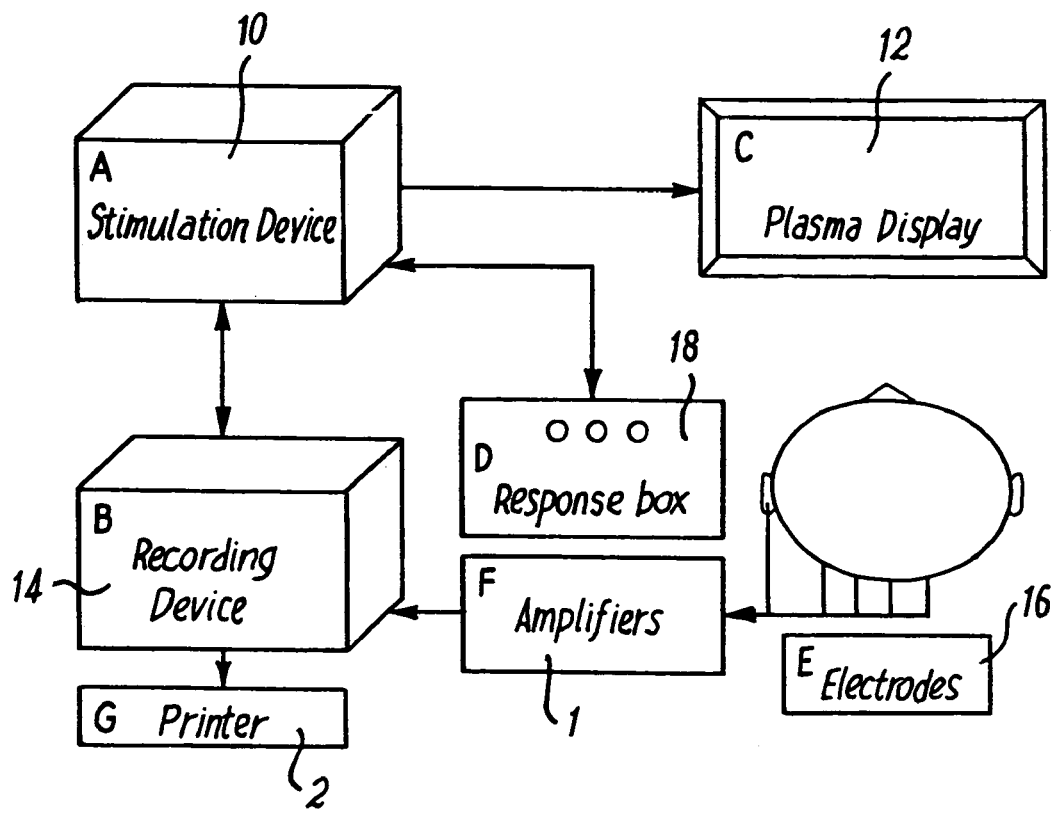
FIG. 4 a block diagram illustrating apparatus in accordance with another embodiment of the present invention.

FIG. 4 shows an alternative arrangement where the second computer 14 acts as a recording device and the signals from the electrodes 16 are passed through an amplifier 1. A printer 2 is also a part of the system. Three types of peripheral stimulus may be used in this case; flickering uniform field, moving radial grating and dynamic noise.

When the invention is applied for psychological testing, as also described further below, the second computer 14 and electrodes 16 are not required, and the apparatus further includes a control unit 18 connected to the first computer 10 and operable by the test subject.

In this example, the inducing stimulus I comprises a circular grating presented in a peripheral sector of the visual field as shown in FIG. 1. This stimulus will be flickering or moving. The test stimulus T may be a checkerboard or visual noise pattern flickering at F Hz.

Figure 3:
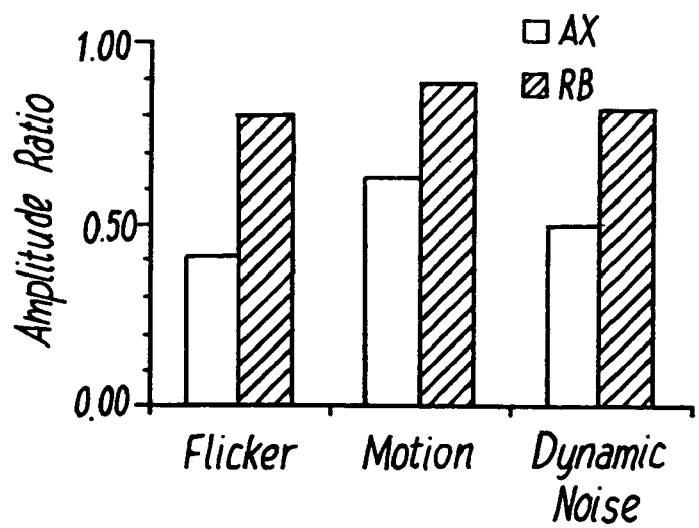
FIG. 3 is a table showing the amplitude ratio between the amplitudes evoked by a test stimulus in the presence and absence of a peripheral stimulus. Open bars=data for a normal observer AX; filled bars=data for a glaucoma patient RB. Three types of peripheral stimuli were used; flickering uniform field, moving radial gratings, and dynamic noise.

The invention may be applied for electrophysiological testing (as shown in FIG. 3) by recording monopolar VEPs elicited by the test stimulus using at least three test electrodes 1 attached on the skin, suitably in a transverse row across the occiput, e.g. at locations O3, Oz and O4 (standard nomenclature for locations on the skull), plus (preferably) a reference electrode, e.g. attached at location Fz. The VEPs from the test electrodes are used to calculate the second spatial derivative of the potential field distribution (Laplacian responses) [refs.10-11]. The Laplacian response, L, may be calculated for example, as $$L = 2Oz - O4 - O3.$$

The generators of the early component of the Laplacian responses are located within the primary visual cortex. Laplacian responses have several advantages as compared to monopolar VEPS. They have higher signal-to-noise ratio; they do not depend on the reference electrode; the alpha activity and electrical signals due to eye movements are eliminated. The Laplacian responses may be recognised in a single sweep.

The Laplacian responses elicited by the test stimulus T are recorded in absence and presence of the inducing stimulus I. The Laplacian responses are attenuated due to long-distance interactions in the visual network. The presence of defects in the area where the inducing stimulus I is displayed might result in a reduced inducing effect. The ratio between the Laplacian responses to the test stimulus T in the absence and presence of the inducing stimulus I can be used to evaluate visual defects in the area where the inducing stimulus I is presented. If the stimulated peripheral area has normal functions, the Laplacian ratio will be less than 1 (i.e. the response to the test stimulus T is affected by the presence or absence of the inducing stimulus I). If the stimulated peripheral area has a visual defect, the Laplacian ratio will be 1 (i.e. the response to the test stimulus T is not affected by the presence or absence of the inducing stimulus I).

The second computer 14 is adapted and programmed to record the signals from the electrodes 16 and to process the signals as described above.

FIG. 3 shows the normal data obtained from a normal observer (AX) and a glaucoma patient (RB) who has reduced sensitivity in both eyes at eccentricity of 10-20 deg. The ratio between the amplitudes of the response to the test stimulus in the presence and absence of a peripheral stimulus is calculated for 3 different types of peripheral stimulation. The results show that these ratios are less than one which might be due to long distance interactions between responses to the test and inducing stimuli. In addition, these ratios are smaller for the normal observer compared to the glaucoma patient. The reduced long-distance interactions effect might be due to the presence of defects in the visual field of the glaucoma patient.

When the invention is applied for psychophysical testing, the contrast threshold for detection of the test stimulus T is measured by the method of adjustment. The test subject has to fixate the centre of the display 12. Two buttons on the control unit (or "response box") 18 enable the subject to decrease and increase the stimulus contrast. Using these buttons the subject varies the contrast until a just noticeable sensation of flicker occurs. Pressing a third button then indicates that the threshold contrast has been reached and the computer 10 will record its value. The stimulus then appears again, but its contrast is randomly selected by the computer 10 to be a multiple (suitably 3-10 times higher or lower) of the measured threshold contrast. The programme repeats the measurements until a suitable number (e.g. 10) thresholds are collected for each experimental condition.

The mean threshold is determined in the absence and presence of the inducing stimulus. The ratio between these two mean threshold measurements may be used for assessment of visual defects in the area where the inducing stimulus is presented, e.g. in a similar manner to that described above for electrophysiological testing.

In summary, long-distance perimetry in accordance with the present invention is based on interactions between the responses to an inducing stimulus I and a test stimulus T. The magnitude of visual defects in the early stages of the visual system is evaluated by the ratio between the responses to the test stimulus T in the absence and presence of the inducing stimulus I. This relative measurement will reduce inter-individual differences, as compared with conventional methods based on "absolute sensitivity" measurements.

The psychophysical test as described above may be applied for patients who can understand and perform the visual task. The electrophysiological test is an objective procedure which requires only fixation at the centre of the display.

According to another aspect, the invention may also be applied for the purpose of measuring internal neural noise. Internal noise may be associated with neural fluctuations of early visual stages. The method of visual evoked potentials (VEPs) in the presence of external noise may be used to evaluate internal noise at different retinal areas.

In this case the stimuli presented by the display apparatus 12 consist of test patterns presented at various parts of the retina/visual field. Laplacian responses to contrast reversals of a test stimulus are recorded without noise and in the presence of several densities of external Gaussian dynamic noise, N.

The power of the test response $R_t$ (squared amplitude) could be expressed as follows:

$$R_t = G_c P_t / (Nadd + G_s N)$$

Where $P_t$ is the contrast energy of the test stimulus,

Nadd is the additive internal noise, $G_c$ is the gain of the response to the central stimulus, $G_s$ is the gain of the response to the peripheral stimulus, and N is the external noise.

The above equation consists of three free parameters: $G_s$, $G_c$ and Nadd, which could be estimated by fitting the data obtained at several noise levels with the equation.

Figure 5:
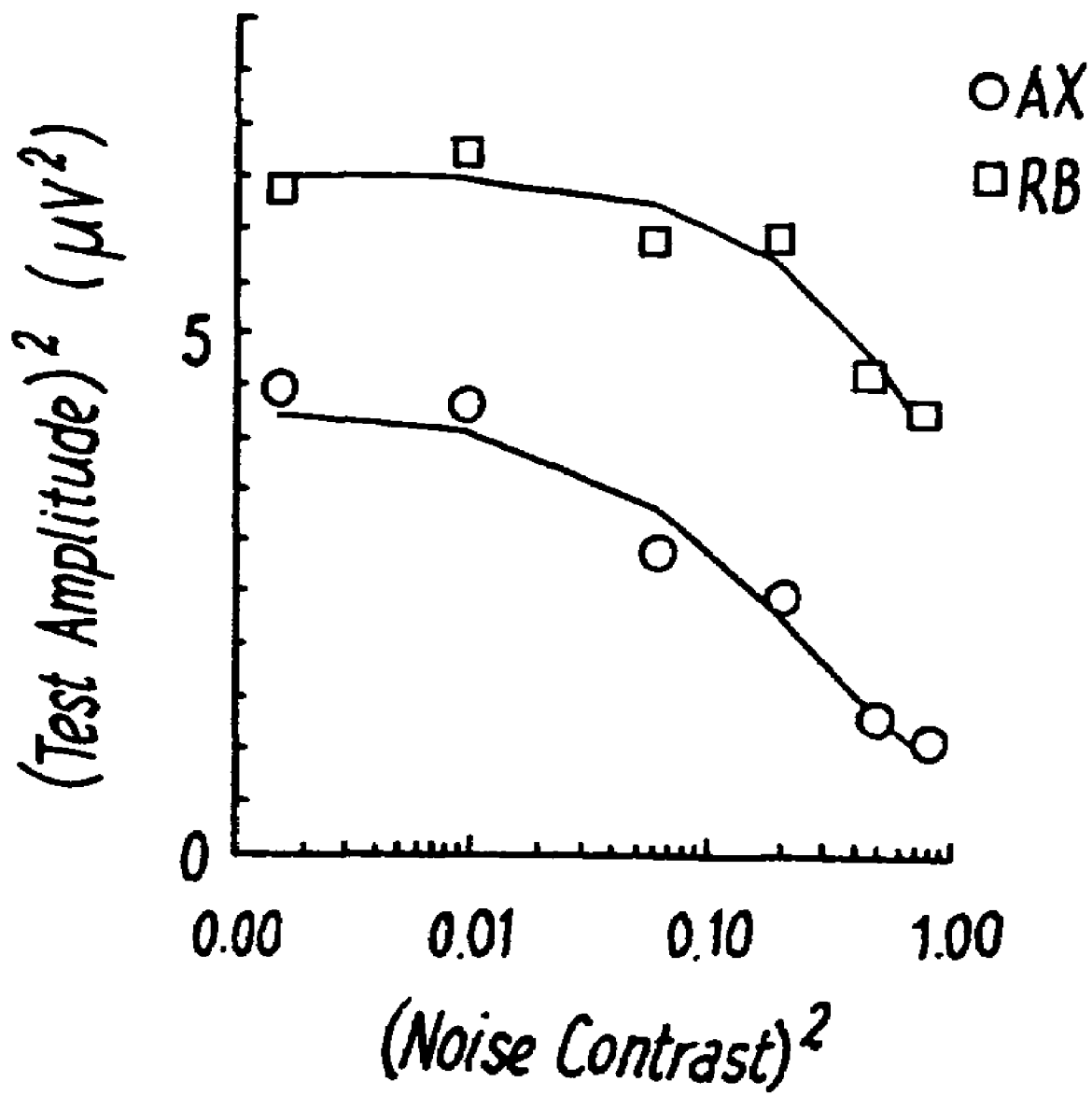
FIG. 5 Squared test amplitude as a function of squared noise contrast. Circles=data for a normal observer AX; square=data for a glaucoma patient RB.

FIG. 5 shows data obtained from the normal observer (circles) and the glaucoma patient (squares). The estimated values for the glaucoma patient are;

$G_c$=1.5 and 3.2

$G_s$=1.5 and 0.3

Nadd=0.4 and 0.5

The glaucoma patient has a reduced gain of the response to the peripheral stimulus as compared to the normal observer, while the internal additive noises are similar. This approach will provide a tool for estimation of internal noise and response gain of different parts of the retina. This might reflect the presence of visual defects in the peripheral retina of this patient.

Thresholds are estimated from the contrast-axis intercept of linear regression approximating the contrast response; i.e. if the VEP response is plotted as a function of contrast, the intercept with the contrast-axis (zero response) indicates the threshold contrast. The threshold signal energy is approximately equal to the threshold contrast squared, multiplied by a constant. Threshold signal energy E as a function of external noise density is fitted by equation:

$$E = (N + Ni)/G \tag{1}$$

The intercept on the noise density axis, Ni, is the equivalent input noise that is a measure of the internal noise. The slope is a measure of the response gain G.

The results provide objective information about internal noise and response gain of different parts of the retina.

Improvements and modifications may be incorporated without departing from the scope of the invention.

What is claimed is:

1. An apparatus for use in the assessment of visual field functions, comprising:
   a visual display device adapted to display visual stimulus patterns; and
   a means for generating visual stimulus patterns within a predetermined visual field and for controlling the display of said visual stimulus patterns by said visual display device; wherein:
   said means for generating visual stimulus patterns is adapted to generate a test stimulus for display in a central region of the visual field and to generate an inducing stimulus for display in a peripheral region of the visual field, and to control the visual display device so as to selectively display the test stimulus alone and in combination with the inducing stimulus in accordance with a predetermined test protocol.

2. An apparatus as in claim 1 wherein the means for generating visual stimulus patterns is a computer.

3. An apparatus as in claim 1 wherein the visual display device is a plasma monitor.

4. An apparatus as in claim 1 further comprising:
   test electrodes for detecting VEPs in response to visual stimuli displayed by said display device; and
   a recording device adapted to record VEP signals from said test electrodes and to compare VEP signals generated in response to the display of the test stimulus alone with VEP signals generated in response to the display of the test stimulus in combination with the inducing stimulus.

5. An apparatus as in claim 4 wherein there are three test electrodes.

6. An apparatus as in claim 1 further comprising means to calculate a Laplacian response (second spatial derivative of the potential field distribution) from each set of VEP signals.

7. An apparatus as in claim 6 wherein the means to calculate a Laplacian response is adapted to calculate a ratio of the Laplacian response for the test stimulus alone and the Laplacian response for the combination of the test stimulus and inducing stimulus.

8. An apparatus as in claim 1 further comprising:
control means operable by a test subject for increasing and decreasing the contrast of the visual stimulus displayed by the display device and for indicating a threshold contrast value.

9. An apparatus as in claim 8 adapted to execute a test protocol comprising: generating a first visual stimulus; recording a first threshold contrast value indicated by the test subject using the control means; displaying the stimulus again with a contrast equal to a randomly selected multiple of the first threshold contrast; recording a second threshold contrast value indicated by the test subject using the control means; repeating this process for a predetermined number of iterations; and calculating a mean threshold contrast value from said first, second and subsequent threshold contrast values.

10. An apparatus as in claim 9 adapted to execute a test protocol comprising: calculating a mean threshold contrast value for a stimulus comprising the test stimulus alone; calculating a mean threshold contrast value for a stimulus comprising the combination of the test stimulus and the inducing stimulus; and calculating the ratio of these two mean threshold contrast values.

11. A method for assessing visual field functions, comprising the steps:
displaying visual stimulus patterns within a predetermined visual field using a visual display device, said visual stimulus patterns comprising a test stimulus displayed in a central region of the visual field and an inducing stimulus displayed in a peripheral region of the visual field; and selectively displaying the test stimulus alone and in combination with the inducing stimulus in accordance with a predetermined test protocol.

12. A method as in claim 11 wherein the visual display device is a plasma monitor.

13. A method as in claim 11 further including the steps:
deploying at least three test electrodes for detecting VEPs in response to visual stimuli displayed by said display device; and
recording VEP signals from said test electrodes and comparing VEP signals generated in response to the display of the test stimulus alone with VEP signals generated in response to the display of the test stimulus in combination with the inducing stimulus.

14. A method as in claim 13 further including the step of calculating a Laplacian response (second spatial derivative) from each set of VEP signals and calculating a ratio of the Laplacian response for the test stimulus alone and the Laplacian response for the combination of the test stimulus and the inducing stimulus.

15. A method as in claim 11 further including the step of; the test subject operating control means to increase and decrease the contrast of the visual stimulus displayed by the display device and to indicate a threshold contrast value.

16. A method as in claim 15 including a test protocol comprising: generating a first visual stimulus; recording a first threshold contrast value indicated by the test subject using the control means; displaying the stimulus again with a contrast equal to a randomly selected multiple of the first threshold contrast; recording a second threshold contrast value indicated by the test subject using the control means; repeating this process for a predetermined number of iterations; and calculating a mean threshold contrast value from said first, second and subsequent threshold contrast values.

17. A method as in claim 16 including the step of; calculating a mean threshold contrast value for a stimulus comprising the test stimulus alone; calculating a mean threshold contrast value for a stimulus comprising the combination of the test stimulus and inducing stimulus; and calculating the ratio of these two mean threshold contrast values.

18. Apparatus for use in the assessment of visual field functions, comprising:
a visual display device adapted to display visual stimulus patterns;
a computer adapted to generate visual stimulus patterns within a predetermined visual field and to control the display of said visual stimulus patterns by said visual display device, said computer being adapted to generate test stimuli for display in a first region of the visual field and to generate visual Gaussian noise patterns of different noise densities for display in at least one other region of the visual field, and to control the value display device so as to selectively display the test stimulus alone and in combination with the noise pattern in accordance with a predetermined test protocol;
at least three test electrodes for detecting VEPs in response to visual stimuli displayed by said display device; and
a computer adapted to record VEP signals from said test electrodes, to calculate a Laplacian response (second spatial derivative) from each set of VEP signals, and to derive an internal neural noise value for said first region of the visual field from said Laplacian responses and associated Gaussian noise densities.

19. A method for assessing visual field functions, comprising:
generating visual stimulus patterns within a predetermined visual field using a visual display device, said stimulus patterns comprising test stimuli displayed in a first region of the visual field and visual Gaussian noise patterns of differing noise densities displayed in at least one other region of the visual field; and selectively displaying the test stimulus alone and in combination with the noise pattern in accordance with a predetermined test protocol;
deploying at least three test electrodes for detecting VEPs in response to visual stimuli displayed by said display device; and
recording VEP signals from said test electrodes, calculating a Laplacian
response (second spatial derivative) from each set of VEP signals, and deriving an internal neural noise value for said first region of the visual field from said Laplacian responses and associated Gaussian noise densities.

* * * * *